United States Patent
Li et al.

(10) Patent No.: US 10,016,148 B2
(45) Date of Patent: Jul. 10, 2018

(54) METHOD AND APPARATUS FOR CORRECTION OF MULTIPLE EM SENSOR POSITIONS

(75) Inventors: Dun Alex Li, Salem, NH (US); Vernon Thomas Jensen, Draper, UT (US); Cristian Atria, Wakefield, MA (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 3193 days.

(21) Appl. No.: 11/528,291

(22) Filed: Sep. 27, 2006

(65) Prior Publication Data

US 2008/0125997 A1    May 29, 2008

(51) Int. Cl.
*A61B 5/06* (2006.01)
*A61B 6/00* (2006.01)
*A61B 90/00* (2016.01)

(52) U.S. Cl.
CPC .............. *A61B 5/06* (2013.01); *A61B 5/062* (2013.01); *A61B 6/547* (2013.01); *A61B 90/39* (2016.02); *A61B 2090/397* (2016.02)

(58) Field of Classification Search
CPC ....... A61B 19/5244; A61B 19/52; A61B 6/12; A61B 6/4014
USPC ....... 600/407, 409, 410, 414, 421, 422, 424; 324/219, 220
See application file for complete search history.

(56) References Cited

U.S. PATENT DOCUMENTS

| | | | |
|---|---|---|---|
| 5,265,610 A | 11/1993 | Darrow et al. | |
| 5,443,066 A | 8/1995 | Dumoulin et al. | |
| 5,676,673 A | 10/1997 | Ferre et al. | |
| 5,829,444 A | 11/1998 | Ferre et al. | |
| 6,119,033 A | 9/2000 | Spigelman et al. | |

(Continued)

FOREIGN PATENT DOCUMENTS

| | | |
|---|---|---|
| JP | 03267054 A | 11/1991 |
| JP | 08196535 A | 4/1996 |

(Continued)

OTHER PUBLICATIONS

Unofficial translation of Japanese Notice of Allowance from JP Application No. 2007-245125 dated Jan. 8, 2014.

(Continued)

*Primary Examiner* — Mark Remaly
(74) *Attorney, Agent, or Firm* — Fletcher Yoder, P.C.

(57) ABSTRACT

In one aspect of the present technique, a method for selecting between a plurality of electromagnetic sensors to correct for one or more field distortions includes, in the presence of an electromagnetic field, acquiring signals representative of the location of a plurality of electromagnetic sensors. The method further includes selecting between the signals from the plurality of electromagnetic sensors based on one or more quality metrics. In another aspect of the present technique, a system for selecting an optimum EM sensor to correct for one or more field distortions includes a plurality of EM sensors and an additional EM sensor for transmitting or receiving signals representative of the location of each of the plurality of EM sensors. The system further includes a controller configured to acquire signals representative of the location of the plurality of EM sensors, and select between the signals from the plurality of EM sensors based on one or more quality metrics.

20 Claims, 4 Drawing Sheets

(56) References Cited

U.S. PATENT DOCUMENTS

| | | |
|---|---|---|
| 6,216,029 B1 | 4/2001 | Paltieli |
| 6,263,230 B1 | 7/2001 | Haynor et al. |
| 6,459,265 B1 | 10/2002 | Lou et al. |
| 6,490,475 B1 | 12/2002 | Seeley et al. |
| 6,493,573 B1 | 12/2002 | Martinelli et al. |
| 6,553,326 B1 | 4/2003 | Kirsch et al. |
| 6,618,653 B2 | 9/2003 | Uehara |
| 6,666,579 B2 | 12/2003 | Jensen |
| 6,669,635 B2 * | 12/2003 | Kessman et al. ............ 600/437 |
| 6,823,207 B1 | 11/2004 | Jensen et al. |
| 6,836,529 B2 | 12/2004 | Jianying et al. |
| 6,854,884 B2 | 2/2005 | Kerrien et al. |
| 6,879,160 B2 * | 4/2005 | Jakab ............................ 324/318 |
| 7,054,407 B1 | 5/2006 | Jianying et al. |
| 7,277,594 B2 | 10/2007 | Hofstetter et al. |
| 7,532,997 B2 | 5/2009 | Li et al. |
| 7,621,169 B2 | 11/2009 | Li et al. |
| 2005/0096557 A1 * | 5/2005 | Vosburgh et al. ............ 600/509 |
| 2006/0061570 A1 | 3/2006 | Liu et al. |
| 2006/0126990 A1 | 6/2006 | Deng et al. |
| 2008/0139883 A1 | 6/2008 | Uchiyama |

FOREIGN PATENT DOCUMENTS

| | | |
|---|---|---|
| JP | 2000014664 A | 1/2000 |
| JP | 2002529133 A | 9/2002 |
| JP | 2002543410 A | 12/2002 |
| JP | 2003019128 A | 1/2003 |
| JP | 2004089421 A | 3/2004 |
| JP | 2005210334 A | 8/2005 |

OTHER PUBLICATIONS

Kindratenko, V., "A survey of electromagnetic position tracker calibration techniques", Virtual Reality: Research, Development, and Applications, vol. 5, No. 3, 2000 pp. 169-182.

* cited by examiner

METHOD AND APPARATUS FOR CORRECTION OF MULTIPLE EM SENSOR POSITIONS

BACKGROUND

The present invention relates generally to tracking systems that use magnetic fields such as for surgical interventions and other medical procedures. More particularly, the present invention relates to techniques for the correction of multiple electromagnetic sensor positions.

Tracking systems have been used to provide an operator (e.g., a physician) with information to assist in the precise and rapid positioning of a medical (e.g., surgical) device in a patient's body. In general, an image is displayed for the operator that includes a visualization of the patient's anatomy with an icon or image representing the device location projected thereon. As the device is positioned with respect to the patient's body, the displayed image is updated to reflect the correct device location. The image of the patient's anatomy may be generated either prior to or during the medical or surgical procedure. Moreover, any suitable medical imaging technique, such as X-ray, computed tomography (CT), magnetic resonance imaging (MRI), positron emission tomography (PET), ultrasound, endoscopy, and optical imaging in the UV, visible, and infrared light spectrums may be utilized.

When used with existing image sets, these previously recorded diagnostic image sets themselves define a three dimensional rectilinear coordinate system, by virtue of their precision scan formation or the spatial mathematics of their reconstruction algorithms. Accordingly, to accurately depict the device position and orientation with the external coordinates of the device being employed, the coordinates of the image should be correlated with the external coordinates of the device being employed.

So that transformations between the respective coordinates may be performed, the various sets of coordinates may be defined by robotic mechanical links and encoders, or more usually, are defined by a fixed patient support, two or more receivers, such as cameras which may be fixed to the support, and a plurality of signaling elements (e.g., electromagnetic sensors) attached to a guide or frame on the device that enable the position and orientation of the device with respect to the patient support and camera frame to be automatically determined by triangulation. Three-dimensional tracking systems employing two video cameras and a plurality of emitters or other position signaling elements have long been commercially available and are readily adapted to such operating room systems. When tracked markers appear in the diagnostic images, it is possible to define a transformation between operating room coordinates and the coordinates of the image.

In one typical tracking system, an electromagnetic ("EM") transmitter is fixed in relation to a patient's body, an EM receiver is fixed in relation to the device, and another EM receiver is fixed in relation to the C-arm of an X-ray fluoroscopy system. The EM transmitter generates an electromagnetic field that is detected by the EM receivers. The signal received by the receiver fixed in relation to the imaging system may be suitably processed to determine the receiver's position and orientation. As this receiver is fixed in relation to the imaging system, the receiver may then be used to determinate the position and orientation of the C-arm. Accordingly, once the signal received by the receiver fixed in relation to the device is processed, the device receiver's position and orientation may be correlated to the imaging system so that the device's position and orientation may be projected onto the diagnostic image.

As will be appreciated, correlation of the patient anatomy with the diagnostic image may be complicated by a number of factors. For example, the presence of field distorting objects (e.g., a C-arm, X-ray detector, or surgical table) may result in distortions in the magnetic field emitted from the EM transmitter and thereby change the magnitude and direction of this field. For example, the presence of a signal from another source, the magnetic field of the eddy current in a conductive object, or the field distorting effect of a ferro-magnetic object can result in these distortions. Unless compensated for, these distortions will result in error in the measured position and orientation of the receivers. While distortion maps are generally used to compensate for certain distortion objects, all the distortions may not be fully compensated for using existing techniques. In other words, there may be some residual distortion that is not compensated for by the distortion map. In addition, as the distance between the transmitter and receiver increases, the signal-to-noise ratio of the sensed data worsens. For example, a transmitter-to-receiver distance of greater than about eighteen inches (approx. 500 mm) may yield unreliable data for certain implementations with existing technologies. As such, if the transmitter-to-receiver distance increases, for example, due to movement of the C-arm, a reliable position and orientation for the C-arm may not be obtained. Without a reliable position and orientation for the C-arm, the device position and orientation may not be accurately projected onto the diagnostic image.

Accordingly, a tracking system utilizing multiple EM receivers fixed in relation to the imaging system may be used to account for some of these complicating factors. For example, the uncompensated distortions may not impact all of the EM receivers in the same manner so that one or more of the receivers may return acceptable data even where one of the receivers does not. Alternatively, dependent upon the position of the C-arm, one of the EM receivers may have an acceptable transmitter-to-receiver distance even if the other receiver does not. However, conventional techniques are generally designed for tracking systems that include a single EM receiver fixed in relation to the C-arm.

Accordingly, there is a need for an improved technique for the correction of magnetic field distortions. Particularly, there is a need for a technique that corrects for magnetic field distortions in tracking systems that utilize multiple EM receivers.

BRIEF DESCRIPTION

The present technique provides an improved technique that corrects for magnetic field distortions in tracking systems that include multiple EM sensors. In one embodiment, the present technique provides a method for selection of an optimum EM sensor to correct for one or more field distortions. The method includes acquiring, in presence of an EM field, signals representative of the location of a plurality of EM sensors. The method further includes selecting between the signals from the plurality of EM sensors based on one or more quality metrics.

In accordance with another embodiment, the present technique provides a system for selecting an optimum EM sensor to correct for one or more field distortions. The system includes a plurality of EM sensors and an additional EM sensor for transmitting or receiving signals representative of the location of each of the plurality of EM sensors. The system further includes a controller configured to acquire signals representative of the location of the plurality of EM sensors, and select between the signals from the plurality of EM sensors based on one or more quality metrics.

In accordance with another embodiment, the present technique provides a computer program, stored on a computer readable medium, for selecting an optimum EM sensor to correct for one or more field distortions. The computer program is constructed and arranged to acquire signals representative of each of a plurality of EM sensors. Moreover, the computer program is also constructed and arranged to select between the signals from the plurality of EM sensors based on one or more quality metrics.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
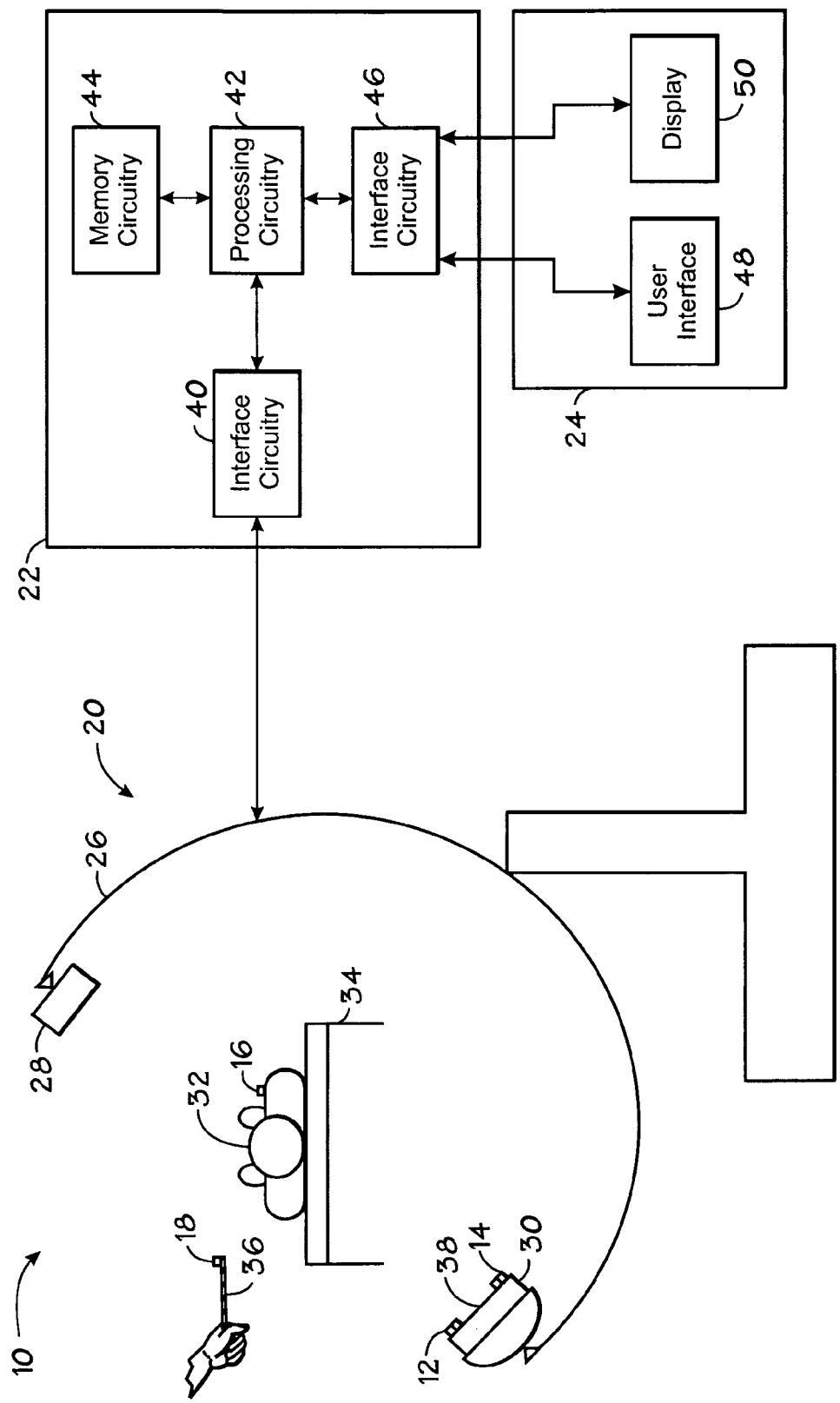
FIG. 1 is a view of an exemplary imaging and tracking system in accordance with one implementation of the present technique.

Referring now to FIG. 1, imaging and tracking system 10 is illustrated. In the illustrated embodiment, imaging and tracking system 10 comprises tracking components that include a plurality of EM sensor assemblies 12, 14, 16, and 18. Further, imaging and tracking system 10 includes an X-ray fluoroscopy system 20 for acquiring and processing image data. As illustrated, imaging and tracking system 10 further includes controller 22 and workstation 24.

As noted above, while specific reference is made in the present discussion to an X-ray imaging system, and particularly to a fluoroscopy system, it should be appreciated that the invention is not intended to be limited to these or to any specific type of imaging system or modality. Accordingly, the technique may be used for tracking, analysis and display of positions of implements in conjunction with other imaging modalities used in real time, or even with images acquired prior to a surgical intervention or other procedure.

X-ray fluoroscopy system 20 is illustrated as a C-arm system that includes a C-arm 26, an X-ray radiation source 28, and an X-ray detector 30. The X-ray radiation source 28 is mounted on the C-arm 26, and the X-ray detector 30 is mounted on the C-arm 26 in an opposing location from the X-ray radiation source 28. While in some systems the X-ray radiation source 28 and the X-ray detector 30 may be fixed, in a typical fluoroscopy system the C-arm 26 allows for movement of the X-ray radiation source 28 and the X-ray detector 30 about the patient 32. In operation, the X-ray radiation source 28 emits a stream of radiation suitable for X-ray fluoroscopy. The X-ray detector 30 receives a portion the stream of radiation from the X-ray source 28 that passes through patient 32 positioned on table 34. The X-ray detector 30 produces electrical signals that represent the intensity of the radiation stream. As those of ordinary skill in the art will appreciate, these signals are suitably acquired and processed to reconstruct an image of features within the subject.

A plurality of EM sensor assemblies may be fixed in relation to the fluoroscopy system. In the illustrated embodiment, first and second sensor assemblies 12, 14 are fixed to calibration assembly 38, which is fixed on the X-ray detector 30 of the X-ray fluoroscopy system 20. Third EM sensor assembly 16 may be fixed in relation to the patient 32. As illustrated, third EM sensor assembly 16 is fixed on the patient 32. Fourth EM sensor assembly 18 may be fixed in relation to the medical (e.g., surgical) device 36. In the illustrated embodiment, second EM sensor assembly 14 is mounted in the operative end of the medical device 36. Device 36 may be may be any suitable device for use in a medical procedure. For example, device 36 may be a drill, a guide wire, a catheter, an endoscope, a laparoscope, a biopsy needle, an ablation device or other similar devices.

Figure 2:
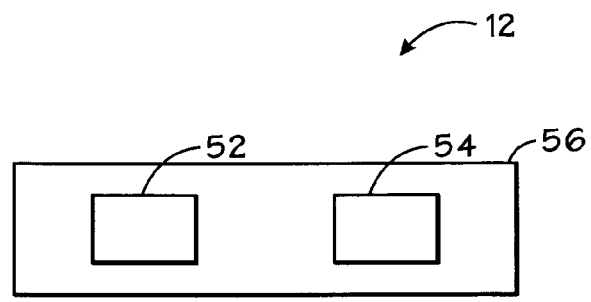
FIG. 2 is a view of an exemplary sensor assembly in accordance with one implementation of the present technique.

In general, each of the EM sensor assemblies 12-18 comprises at least one EM sensor. In one particular implementation, each of the EM sensor assemblies 12-18 may comprise two EM sensors for monitoring the integrity of the electromagnetic field. FIG. 2 illustrates first EM sensor assembly 12 as comprising two EM sensors in accordance with one embodiment of the present technique.

Referring again to FIG. 1, the one or more EM sensors included in each of the EM sensor assemblies 12-18 may be implemented as EM receivers or EM transmitters, as will be appreciated by those of ordinary skill. In one embodiment, third EM sensor assembly 16 may include EM transmitter, while the remaining EM sensor assemblies 12, 14, and 18 may each include an EM receiver. In this embodiment, the signals sensed by fourth EM sensor assembly 18 that is fixed in relation to the device 36 may be used to determine the location of the device 36, for example, the position and orientation, including the X-,Y-and Z- coordinates and the pitch, yaw, and roll angles. Likewise, the signals sensed by the first and second EM sensor assemblies 12, 14 may be used to determine the location of the respective sensor assembly. As will be appreciated, the mutual inductance of two EM sensors is the same, regardless as to which is the receiver and the transmitter. Therefore, relative positioning and functionality of the EM receivers and transmitters may be reversed. For example, an EM receiver may be fixed in relation to the patient 32 while EM transmitters may be fixed in relation to the device 36 and the C-arm 26.

Any suitable technique for using an EM sensor for generating a field in which position detection may be achieved may be utilized with the present technique. By way of example, the third EM sensor assembly 16 may be implemented as a field generator that includes three orthogonally disposed magnetic dipoles (e.g., current loops or electromagnets). Electromagnetic fields generated by each of the dipoles are distinguishable from one another in phase, frequency, time division multiplexing, and the like. As those of ordinary skill in the art will appreciate, the near-field characteristics of the electromagnetic fields may be used for coordinate determination.

In the illustrated embodiment, controller 22 includes interface circuitry 40 for receiving tracking and imaging data, processing circuitry 42, memory circuitry 44, and workstation interface circuitry 40 for communicating with workstation 24. As will be appreciated, one or more computers may be used to implement controller 22. In general, processing circuitry 42, which will typically include a digital signal processor, a CPU or the like, may process the tracking data so that the location of the device 36 may be projected onto the diagnostic image. In addition, processing circuitry 42 also may process the imaging data to reconstruct the data into a meaningful diagnostic image. Memory circuitry 44 may serve to save the imaging and tracking data as well as other system parameters.

As illustrated, workstation 24 includes user interface 48 and a display 50. User interface 48 may include a keyboard and/or mouse, as well as other devices such as printers or other peripherals for reproducing hardcopies of the reconstructed images. Display 50 may include a first screen for displaying a previously acquired image and second screen for displaying one or more intra-operative images.

As previously mentioned, in one particular embodiment, each of the EM sensor assemblies 12-18 may comprise two EM sensors for monitoring the integrity of the EM field. FIG. 2 illustrates first EM sensor assembly 12 as comprising two EM sensors, in accordance with one embodiment of the present technique. In the illustrated embodiment, the first EM sensor assembly 12 comprises primary EM sensor 52 and reference EM sensor 54. Each of the EM sensors 52, 54 is mounted on body 56. As the distance between the two sensors in the assembly is fixed, the reference EM sensor 54 may be used to monitor the integrity of the EM field, as well as the proper operation of the system 10 itself. Any suitable technique may used to monitor the integrity of the EM field using the primary EM sensor 52 and/or the reference EM sensor 54. Use of sensors assemblies that comprise two sensors for field integrity detection is described in more detail in U.S. Pat. No. 5,676,673, which is incorporated herein in its entirety by reference.

Figure 3:
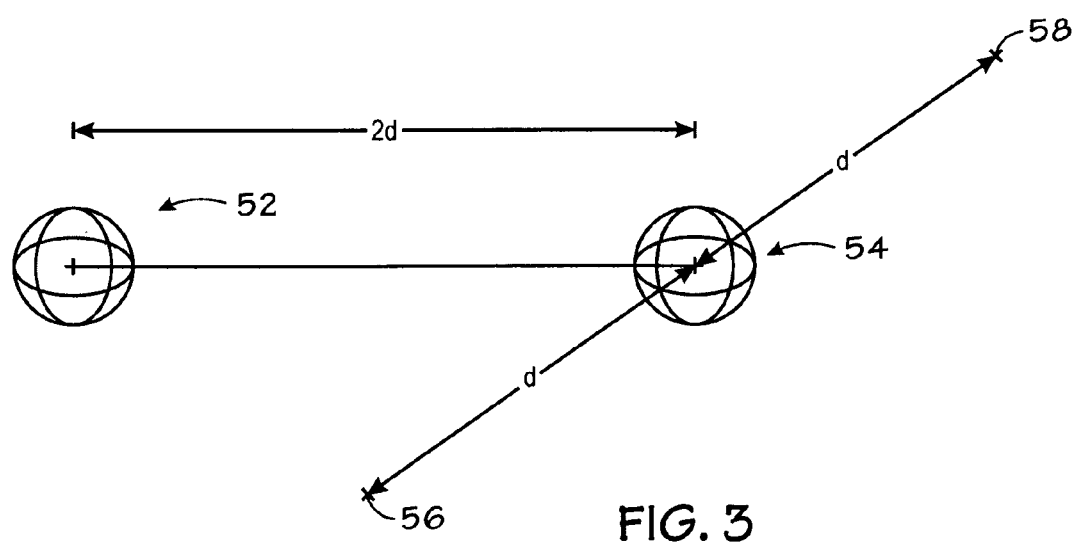
FIG. 3 is a view illustrating the use of virtual points in combination with an exemplary sensor assembly for error detection in accordance with one implementation of the present technique.

In accordance with one particular embodiment, the integrity of the electromagnetic field may be monitored by monitoring the location of two or more virtual points. As illustrated by FIG. 3, a first virtual point 56 may be defined between the X-Z planes defined by the two sensors, and a second virtual point 58 may be defined outside the X-Z plane defined by the two sensors. In one embodiment, the magnitude of the vector from the reference EM sensor 54 to the first virtual point 56 may be the same as the magnitude of the vector from the reference EM sensor 54 to the second virtual point 58, but in the opposite direction. This magnitude may be approximately one half the distance between the primary EM sensor 52 and the reference EM sensor 54. The locations of these two virtual points 56, 58 may be continuously calculated and compared with established locations determined in a distortion free environment, such as during factory calibration. If the distance between the measured location and the established location of either virtual point is greater than a threshold value, then a field integrity violation may be reported. This distance between the measured location and the established location for the virtual points will be referred to herein as the "field integrity value."

As those of ordinary skill in the art will appreciate, signals representative of the location of the first and second EM sensor assemblies 12, 14 may be acquired. For example, in instances where the first and second EM sensor assemblies 12, 14 serve as EM receivers, the signals may be received from the third EM sensor assembly 16 fixed in relation to the patient 32, which may serve as a transmitter. Alternatively, in instances where the first and second EM sensor assemblies 12, 14 serve as EM transmitters, the signals are transmitted to the third EM sensor assembly 16 fixed in relation to the patient 32, which may serve as a receiver. The acquired EM signals then may be suitably processed to determine the location of each of the EM sensor assemblies, for example, the position and orientation, including the X, Y and Z coordinates and the pitch, yaw and roll angles. As the first and second EM sensor assemblies 12, 14 are fixed in relation to the C-arm 26, once the location of these sensor assemblies are determined, the position and orientation of the C-arm 26 may be determined.

As will be appreciated, however, the presence of field distorting objects in the clinical environment will typically result in distortions in the electromagnetic field. For example, the field distorting objects may be tables, fixtures, tools, electronic equipment, one or more components of an imaging system (e.g., a C-arm). While these distortions may be compensated for using certain techniques, such as distortion maps (e.g., lookup tables that cross reference distorted and undistorted sensor position and orientation), there may be some distortion that is not compensated for by these techniques. In addition, magnetic field strength and the transmitter-to-receiver distance may vary for each of the first and second EM sensor assemblies 12, 14. Accordingly, because the present system 10 includes a plurality of EM sensor assemblies (such as first and second sensor assemblies 12, 14) fixed in relation to the C-arm 26, two different locations for the C-arm 26 can be determined due to, among other things, magnetic field distortions. In other words, a first C-arm position and orientation can be determined based on the determined location of the first sensor assembly 12 and a second C-arm position and orientation can be determined based on the location of the second sensor assembly 14. Because projection of the device location onto the anatomical image is based, at least in part, on the determined position and orientation of the C-arm 26, the precise device location represented on the image will vary based on which sensor assembly is used to determine the C-arm position and orientation.

It should be noted that the device location should be accurately projected onto the anatomical image. Accordingly, an embodiment of the present technique provides a technique for selecting an optimal EM sensor from a plurality of EM sensors, such as first and second EM sensor assemblies 12, 14. Although reference is made herein to distinguishing and selecting between sensors, those skilled in the art will recognize that in practice, the systems described herein will typically acquire signals from all sensors, then select which of the signals or sensors produces the most desired or reliable signals for use in tracking and navigation functions. Based, at least in part on the selected EM sensor, the device location may be projected onto the anatomical image.

Figure 4:
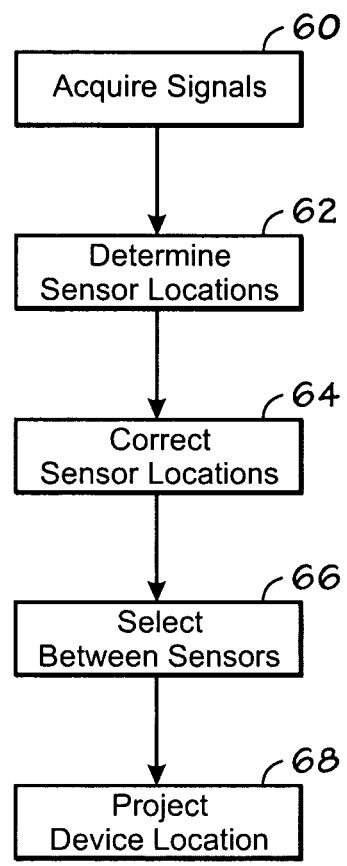
FIG. 4 is a block diagram of an exemplary technique for selecting an optimum EM sensor, in accordance with one implementation of the present technique.

Referring now to FIG. 4, an exemplary technique for selecting an optimal EM sensor from a plurality of EM sensors in accordance with embodiments of the present invention is illustrated. As indicated in block 60, signals representative of the location of each of a plurality of EM sensors may be acquired in the presence of a magnetic field. The plurality of EM sensors may be fixed in relation to a C-arm 26. By way of example, signals representative of the location of the first and second assemblies 12, 14 may be acquired. In instances where the first and second EM sensor assemblies 12, 14 serve as an EM receiver, the signals may be received by the first and second EM sensor assemblies 12, 14 from the third EM sensor assembly 16 fixed in relation to the patient, which may serve as a transmitter. For example, the third EM sensor assembly may comprise a three-axis set of transmitter coils, and each of the first and second sensor assemblies 12, 14 may comprise a three-axis set of receiver coils. Each transmitter coil may be energized to generate a time-varying magnetic field. Measurable voltages are then induced in the receiver coils, in response to this time-varying magnetic field. Accordingly, the mutual inductance may be measured by the ratio of the rate of change of current in the transmitter coil and the induced voltage in the receiver coil. Alternatively, in instances where the first and second EM sensor assemblies 12, 14 serve as EM transmitters, the signals may be transmitted to the third EM sensor assembly 16 fixed in relation to the patient, which may serve as a receiver.

The acquired EM signals may then be suitably processed to determine the location of each of the plurality of EM sensors, as indicated in block 62. For example, the acquired signals may be processed to determine the position and orientation of each of the first and second sensor assemblies 12, 14, including the X, Y and Z coordinates and the pitch, yaw, and roll angles.

In one particular implementation, the determined location of each of the plurality of EM sensors may be corrected for distortions, as indicated in block 64. As those of ordinary skill in the art will appreciate, a distortion map may be used for this distortion correction. In one embodiment, the distortion map may include a look-up table that cross-references undistorted sensor position and orientations with, for example, distorted sensor position and orientations or distorted mutual inductances.

As previously mentioned, the plurality of EM sensors may be fixed in relation to a C-arm 26. Accordingly, a position and orientation of the C-arm 26 may be determined with respect to each of the plurality of EM sensors. Because projection of the device location onto the anatomical image is based, at least in part, on the determined position and orientation of the C-arm 26, the precise device location projected onto the image will vary based on which of the plurality of EM sensors is used to determine the C-arm position and orientation.

Accordingly, the present technique selects between the plurality of EM sensors based on one or more quality metrics, as indicated by block 66. Once the EM sensor is selected, the C-arm position and orientation may then be determined based on this selected sensor. In turn, the device location may then be projected (block 68) onto the anatomical image based, at least in part, on the selected EM sensor. For example, the selected sensor may be used in the transformation from the device coordinate system to the image coordinate system. The transformation may start with a calibration of the device tip to the sensor coordinate system that is fixed in relation to the patient, such as third EM sensor assembly 16. The device tip then may then be transformed into the selected sensor coordinate system fixed in relation to the imaging system, such as first sensor assembly 14 or second sensor assembly 16. Next, the device tip position may then be projected on to the 2D or 3D image based the pre-determined transformation between the selected C-arm sensor to the image coordinate system.

Any of a variety of quality metrics may be used in selecting the optimal EM sensor, including the transmitter-to-receiver distance, the magnetic field strength, the integrity of the EM field, and combinations thereof. One quality metric that may be used in selecting the optimal EM sensor may be the transmitter-to-receiver distance. As will be appreciated, as the transmitter-to-receiver distance increases, the signal-to-noise ratio worsens. In one embodiment, the EM sensor of the plurality of EM sensors with the shortest transmitter-to-receiver distance may be selected. In another embodiment, the transmitter-to-receiver distance for each of the plurality of the EM sensors may be compared to a distance threshold. In one particular embodiment, a distance threshold of in the range of from about 3 inches (approx. 75 mm) to about 18 inches (approx. 500 mm) may be used. However, as those skilled in the art will appreciate, the distance threshold for a particular receiver-transmitter arrangement will vary based on a number of factors and may even exceed 18 inches for a particular implementation.

By way of example, the transmitter-to-receiver distance for the first sensor assembly 12 may be compared to the distance threshold, as well as the transmitter-to-receiver distance for the second sensor assembly 14. As will be appreciated, this distance is the distance from the EM sensor contained on a particular sensor assembly to the associated EM transmitter or EM receiver, as appropriate. If the sensor assembly contains two EM sensors, for example, a primary EM sensor and a reference EM sensor, as discussed above, the transmitter-to-receiver distance may be determined from the primary EM sensor. In one embodiment, if the transmitter-to-receiver distance for the particular EM sensor exceeds the distance threshold, that particular EM sensor may not be selected. If the transmitter-to-receiver distance for each of the plurality of EM sensors exceeds the distance threshold, the EM sensor with the shortest transmitter-to-receiver distance may be selected. In some embodiments, the transmitter-to-receiver distance for at least two sensors of the plurality of EM sensors may be within the distance threshold. In these embodiments, an additional quality metric may then be used for selecting the optimal EM sensor. In one particular embodiment, the EM sensor with the shortest transmitter-to-receiver distance may be selected.

In addition to the transmitter-to-receiver distance, the magnetic field strength also may be used in selecting the optimum EM sensor from the plurality of EM sensors. In one embodiment, the magnetic field strength may be determined using each of the plurality of EM sensors. For example, the magnetic field strength may be determined using the first EM sensor assembly 12 and also may be determined using the second EM sensor assembly 14. Once determined, the magnetic field strength as measured for each of the plurality of EM sensors may be compared to the magnetic field strength of the other EM sensors of the plurality of EM sensors. In one embodiment, the EM sensor with the strongest magnetic field strength may be selected as the optimal sensor. In some embodiments, the determined magnetic field strength may be used in conjunction with one of the other quality metrics, such as transmitter-to-receiver distance and EM field integrity, in selecting the optimal EM sensor from the plurality of the EM sensors.

Moreover, the integrity of the EM field also may be used in selecting the optimum EM sensor from the plurality of EM sensors. As previously mentioned, in some embodiments, the integrity of the EM field may be monitored by including a reference EM sensor in each of the EM sensor assemblies that is fixed with respect to the primary EM sensor in the respective sensor assembly. In accordance with one embodiment, the integrity of the EM field may be monitored by monitoring the location of two or more virtual points with respect to each of the EM sensors in the particular EM assembly. Using these virtual points, a field integrity value may be determined for each virtual point with respect to a particular EM sensor in the assembly. In accordance with one particular implementation, the field integrity value for a particular EM sensor may be compared to a preset threshold. By way of example, the field integrity value for each of the virtual points monitored with respect to the first sensor assembly 12 may be compared to a preset threshold, as well as the field integrity values with respect to the second sensor assembly. In one embodiment, if the field integrity value for the particular EM sensor exceeds the preset threshold, that particular EM sensor will not be selected. In some embodiments, the field integrity value for at least two sensors of the plurality of EM sensors may be less than the preset threshold. In these embodiments, an additional quality metric may then be used to select the optimal EM sensor. In some embodiments, the field integrity value may be used in conjunction with one of the other quality metrics, such as the magnetic field strength and the transmitter-to-receiver distance and the EM field integrity, in selecting the optimal EM sensor from the plurality of the EM sensors.

Figure 5:
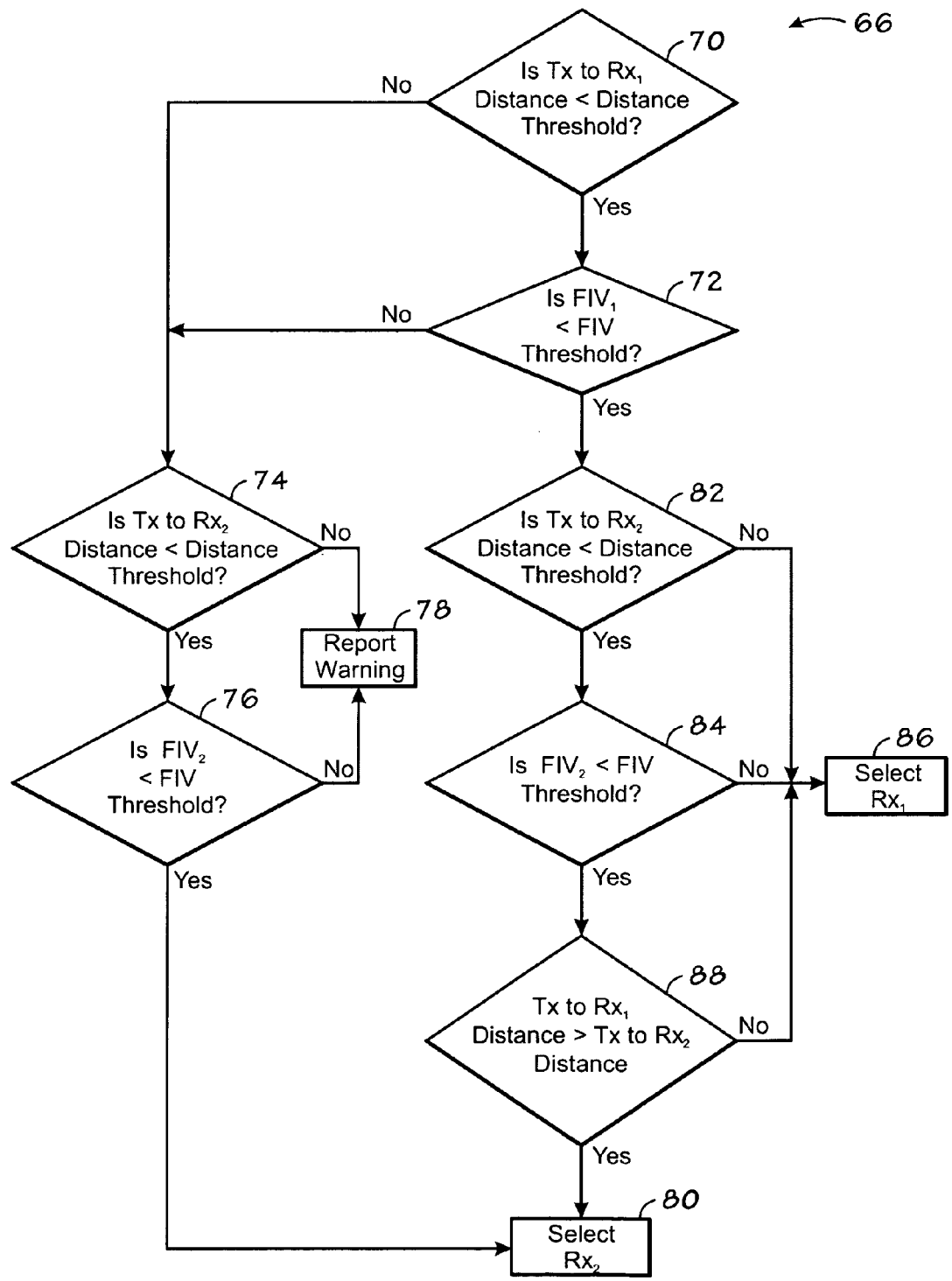
FIG. 5 is a block diagram of an exemplary technique using two or more quality metrics to select an optimum EM sensor in accordance with one implementation of the present technique.

Referring now to FIG. 5, a flow chart is depicted for selecting between the plurality of EM sensors based on the one or more quality metrics, generally referred to by reference numeral 66. In the illustrated embodiment, the transmitter-to-receiver distance and the field integrity are used to select between the first sensor assembly 12 and the second sensor assembly 14. To select between these two sensors assemblies, the both of the sensor assemblies are compared to a series of quality metrics. As indicated by block 70, the transmitter-to-receiver distance for the primary sensor in first EM sensor assembly 12 is first compared to the distance threshold. If the transmitter-to-receiver distance for the first sensor assembly 12 is less than the distance threshold, the field integrity value for the first sensor assembly 12 is then compared (block 72) to a preset threshold.

In the illustrated embodiment, if the transmitter-to-receiver distance for the first sensor assembly 12 is greater than the distance threshold or the field integrity value for the first sensor assembly 12 is greater than the preset threshold, the first sensor assembly 14 will not be selected and the present technique moves to block 74. Accordingly, the second sensor assembly 14 must then be compared to the series of quality metrics. As indicated by block 74, the transmitter-to-receiver distance for the second sensor assembly 14 is first compared to the distance threshold. If the transmitter-to-receiver distance for the second sensor assembly 14 is less than the distance threshold, the field integrity value for the second sensor assembly 14 is then compared (block 76) to a preset threshold. For the second sensor assembly 14, if either the transmitter-to-receiver distance as determined in block 74, or the field integrity value as determined in block 76 is greater than their respective thresholds, the second sensor assembly may not be selected. Rather, a warning may be reported, as indicated in block 78. However, if both of these quality metrics for the second sensor assembly 14 are less than their respective thresholds, the second sensor assembly may be selected, as indicated in block 80.

Moreover, if the quality metrics for the first sensor assembly 12 are both less than their respective thresholds, as determined in blocks 70 and 72, the second sensor assembly 14 may then be compared to the series of quality metrics. As indicated by block 82, the transmitter-to-receiver distance for the primary sensor in the second sensor assembly 14 is first compared to the distance threshold. If the transmitter-to-receiver distance for the second sensor assembly 14 is less than the distance threshold, the field integrity value for the second sensor assembly 14 is then compared (block 84) to a preset threshold. For the second sensor assembly 14, if either the transmitter-to-receiver distance as determined in block 82, or the field integrity value as determined in block 84 is greater than their respective thresholds, the second sensor assembly may not be selected. Rather, the first sensor assembly 12 will be selected (block 86), as the quality metrics for that particular sensor assembly were found to be within the thresholds of the quality metrics, as determined in blocks 70 and 72. However, if both of these quality metrics for the second sensor assembly are less than their respective thresholds, an additional metric may be used to select between these two sensor assemblies. For example, the transmitter-to-receiver distance for the first sensor assembly 12 may be compared (block 88) to the transmitter-to-receiver distance for the second sensor assembly. As illustrated, the sensor assembly with the shortest transmitter-to-receiver distance may be selected. As will be appreciated, due to a better signal-to-noise ratio, the sensor assembly with the shorter transmitter-to-receiver distance may be selected. For example, if this distance for the first sensor assembly 12 is shorter than this distance for the second sensor assembly 14, then the first sensor assembly may be selected, as indicated in block 86. If this distance for the first sensor assembly 12 is not shorter than this distance for the second sensor assembly 14, then the second sensor assembly may be selected, as indicated in block 80.

It should be noted that, while the above-described embodiments describe selecting a particular EM sensor of the plurality, it should be understood that selecting between the plurality of the EM sensors may also encompass the application of a weighting algorithm to the measurements from each of the sensors. For example, a weighting algorithm may be applied to the determined device position in the image coordinate system for each of the plurality of EM sensors. In one particular implementation, the transmitter-to-receiver distances may be used as the weights for the weighting algorithm. For example, the weights $w_1$ and $W_2$ used for the first and second sensor assemblies 12 and 14, respectively, may be defined as $$w_1 = \frac{d_2^2}{d_1^2 + d_2^2}$$

$$w_2 = \frac{d_1^2}{d_1^2 + d_2^2}$$

where $d_1$), and $d_2$ are the transmitter-to-receiver distances from the sensor assembly 16 fixed in relation to the patient to the sensor assemblies 12 and 14 fixed in relation to the imaging system, respectively.

The device position $\overline{X}$ in the image coordinate system thus can be determined by combining the device projection information $\overline{X}_1$ and $\overline{X}_2$ acquired by both sensor assemblies $$\overline{X} = w_1 \overline{X}_1 + w_2 \overline{X}_2$$

As will be appreciated, by weighting and combining measurements from each sensor assembly may substantially improve the robustness of the navigation system.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for selecting between a plurality of electromagnetic sensors to locate a device, comprising:

in the presence of an electromagnetic field, acquiring signals representative of the location of each of a plurality of electromagnetic sensors;

selecting between the sensors from the plurality of electromagnetic sensors based on one or more quality metrics, each of the sensors emitting signals in response to the electromagnetic field;

determining the location of a device in the electromagnetic field based upon the signals from the selected sensor; and projecting the device location on an image of a subject in the electromagnetic field and displaying the image and projection.

2. The method of claim 1, wherein the one or more quality metrics are selected from one or more of a transmitter-to-receiver distance, an electromagnetic field strength, or an electromagnetic field integrity.

3. The method of claim 1, wherein the selecting between the sensors from the plurality of electromagnetic sensors comprises using a weighting algorithm.

4. The method of claim 1, wherein the selecting between the sensors from the plurality of electromagnetic sensors comprises determining a transmitter-to-receiver distance for each of the plurality of electromagnetic sensors.

5. The method of claim 4, wherein the selecting between the sensors from the plurality of electromagnetic sensors comprises comparing the transmitter-to-receiver distance for each of the electromagnetic sensors to the transmitter-to-receiver distance for the remainder of the plurality of electromagnetic sensors.

6. The method of claim 4, wherein the selecting between the sensors from the plurality of electromagnetic sensors comprises comparing the transmitter-to-receiver distance for each of the plurality of electromagnetic sensors to a distance threshold.

7. The method of claim 1, wherein the selecting between the sensors from the plurality of electromagnetic sensors comprises determining a field integrity value for each of the plurality of electromagnetic sensors.

8. The method of claim 1, wherein the selecting between the sensors from the plurality of electromagnetic sensors comprises determining an electromagnetic field strength at each of the plurality of electromagnetic sensors.

9. The method of claim 1, comprising determining the location of each of the plurality of electromagnetic sensors based on the acquired signals.

10. The method of claim 1, comprising determining a position and orientation of the device based in part on the selection between the plurality of electromagnetic sensors.

11. The method of claim 1, comprising monitoring the integrity of the electromagnetic field.

12. The method of claim 1, comprising fixing the plurality of electromagnetic sensors in relation to an imaging system.

13. A system for selecting an optimum electromagnetic sensor to locate a device, comprising:

a plurality of electromagnetic sensors;

an additional electromagnetic sensor configured to generate an electromagnetic field, wherein each of the sensors of the plurality of electromagnetic sensors is configured to emit signals in response to the electromagnetic field;

a controller configured to acquire signals representative of the location of the plurality of electromagnetic sensors, to select between the sensors from the plurality of electromagnetic sensors based on one or more quality metrics, to determine the location of a device in the electromagnetic field based upon the signals from the selected sensor, and to project the device location on an image of a subject in the electromagnetic field; and a display to display the image and projection.

14. The system of claim 13, comprising an imaging system, and wherein the plurality of electromagnetic sensors are fixed in relation to the imaging system.

15. The system of claim 13, wherein the additional electromagnetic sensor is fixed in relation to the subject.

16. The system of claim 13, wherein the one or more quality metrics are selected from one or more of a transmitter-to-receiver distance, an electromagnetic field strength, or an electromagnetic field integrity.

17. The system of claim 13, wherein the controller is further configured to determine the location of each of the plurality of electromagnetic sensors based on the acquired signals.

18. The system of claim 13, wherein the controller is further configured to correct the determined location of each of the plurality of electromagnetic sensors for distortions.

19. The system of claim 13, wherein the controller is further configured to determine a position and orientation of the device based in part on the selection between the plurality of electromagnetic sensors.

20. A computer program, stored on a non-transitory computer readable medium, for selecting an optimum electromagnetic sensor to locate a device, the program constructed and arranged to:

acquire signals representative of the location of each of a plurality of electromagnetic sensors, each of the sensors emitting signals in response to an electromagnetic field;

select between the sensors from the plurality of electromagnetic sensors based on one or more quality metrics;

determine the location of a device in the electromagnetic field based upon the signals from the selected sensor; and project the device location on an image of a subject in the electromagnetic field and display the image and projection.

* * * * *